(12) United States Patent
Clay et al.

(10) Patent No.: US 10,520,634 B2
(45) Date of Patent: Dec. 31, 2019

(54) DOWNHOLE DETECTION TOOL

(71) Applicant: Guardian Global Technologies Limited, Pyle (GB)

(72) Inventors: Oliver Clay, Pontyclun (GB); Iain Maxted, Cowbridge (GB); Jonathan Gore, Finchampstead (GB); Alexander Grigorov, Porthcawl (GB); Paul Moss, Pontyclun (GB)

(73) Assignee: GUARDIAN GLOBAL TECHNOLOGIES LIMITED, Houston, TX (US)

( * ) Notice: Subject to any disclaimer, the term of this patent is extended or adjusted under 35 U.S.C. 154(b) by 0 days.

(21) Appl. No.: 15/027,521

(22) PCT Filed: Oct. 7, 2014

(86) PCT No.: PCT/GB2014/053022
§ 371 (c)(1),
(2) Date: Apr. 6, 2016

(87) PCT Pub. No.: WO2015/052508
PCT Pub. Date: Apr. 16, 2015

(65) Prior Publication Data
US 2016/0245947 A1 Aug. 25, 2016

(30) Foreign Application Priority Data
Oct. 7, 2013 (GB) .................................. 1317673.0

(51) Int. Cl.
*G01V 3/28* (2006.01)
*E21B 47/09* (2012.01)
(Continued)

(52) U.S. Cl.
CPC ................ *G01V 3/28* (2013.01); *E21B 47/09* (2013.01); *E21B 47/0905* (2013.01); *G01N 27/902* (2013.01); *E21B 43/116* (2013.01)

(58) Field of Classification Search
CPC ......... G01V 3/12; E21B 43/11; E21B 47/024; E21B 47/09
See application file for complete search history.

(56) References Cited

U.S. PATENT DOCUMENTS 3,543,144 A * 11/1970 Walters ............... E21B 47/0905
324/221
3,940,689 A 2/1976 Johnson, Jr.
(Continued)

FOREIGN PATENT DOCUMENTS

EP 0 816 838 A1 1/1998

OTHER PUBLICATIONS

International Search Report, PCT/GB2014/053022, dated May 20, 2015, pp. 12.

*Primary Examiner* — Huy Q Phan
*Assistant Examiner* — Adam S Clarke
(74) *Attorney, Agent, or Firm* — Mossman, Kumar & Tyler, PC

(57) ABSTRACT

The present invention concerns a downhole cable or control line detection tool. More particularly, but not exclusively, this invention concerns a method and apparatus for the downhole detection of a cable or control line associated with the external wall of a well casing. A downhole tool for the detection of downhole cable or control lines is provided. The downhole tool comprises an eddy current sensor, the eddy current sensor being arranged to be proximate to the internal wall of a well casing. The eddy current sensor is arranged for pulsed operation. The downhole tool further comprises a mechanism for rotating the eddy current sensor, with an axis (Continued)

of rotation parallel with the longitudinal axis of a well casing.

23 Claims, 3 Drawing Sheets

(51) Int. Cl.
*G01N 27/90* (2006.01)
*E21B 43/116* (2006.01)

(56) References Cited

U.S. PATENT DOCUMENTS

| | | | | |
|---|---|---|---|---|
| 6,087,830 | A * | 7/2000 | Brandly | G01M 3/005 |
| | | | | 324/220 |
| 6,456,066 | B1 * | 9/2002 | Burd | G01N 27/902 |
| | | | | 324/220 |
| 6,924,640 | B2 * | 8/2005 | Fickert | E21B 47/082 |
| | | | | 324/220 |
| 2003/0117142 | A1 * | 6/2003 | Amini | G01V 3/28 |
| | | | | 324/339 |
| 2006/0202686 | A1 * | 9/2006 | Barolak | E21B 47/082 |
| | | | | 324/232 |
| 2009/0166035 | A1 | 7/2009 | Almaguer | |
| 2010/0207711 | A1 | 8/2010 | Estes | |
| 2013/0193953 | A1 | 8/2013 | Yarbro et al. | |
| 2014/0360289 | A1 * | 12/2014 | Georgeson | G01D 11/30 |
| | | | | 73/866.5 |

* cited by examiner

DOWNHOLE DETECTION TOOL

FIELD OF THE INVENTION

The present invention concerns a downhole cable or control line detection tool. More particularly, but not exclusively, this invention concerns a method and apparatus for the downhole detection of a cable or control line associated with the external wall of a well casing.

BACKGROUND OF THE INVENTION

Downhole cables or control lines typically run along the outer wall of an oil or gas well casing. Control lines may be used to provide control information from a surface control unit to downhole devices, and/or provide production information from a downhole device to a surface control unit. It is essential that the downhole cables and control lines are not damaged as a result of well perforation or other ballistics activities.

During well operation, it is common to perforate the well casing in order to create a flow path for the oil and/or gas to flow into the well. This may be done by introducing downhole tools including perforating guns which fire explosive charges through the well casing. As perforations are generally made circumferentially in the well casing, there is a risk that a downhole cable or control line on the outside of the well casing is damaged or broken by an explosive charge. This may render the well inoperable, or at least make operation of the well more difficult.

The present invention seeks to mitigate the above-mentioned problems.

SUMMARY OF THE INVENTION

The present invention provides, according to a first aspect, a downhole tool for the detection of downhole cables or control lines, the downhole tool comprising:

an eddy current sensor, the eddy current sensor being arranged to be in proximity to the inner wall of a well casing, the eddy current sensor arranged for pulsed operation, and a mechanism for rotating the eddy current sensor, with an axis of rotation parallel with the longitudinal axis of a well casing.

The eddy current sensor may be located within 10 mm of the well casing, more preferably within 5 mm of the well casing, and more preferably again within 3 mm of the well casing.

The use of the term "eddy current sensor" is as would be understood by a person skilled in the art. Eddy current sensors, also known as inductive sensors, enable a non-contact measurement to be taken of conductive materials. The eddy current sensor may be arranged to produce an alternating electrical current. This alternating electrical current creates an alternating magnetic field, which results in the creation of eddy currents in the target material. In turn, the eddy currents produce a magnetic field which opposes the field that has been created by the eddy current sensor. How the two magnetic fields interact is detected by the eddy current sensor. The magnitude of the eddy currents generated and therefore the magnitude of the opposing magnetic field is dependent on the distance between the eddy current sensor and the target material and the electrical and magnetic properties of the target material. Therefore, eddy current sensors may be used for example, as known in the prior art, for detecting variations in metal thickness. The term eddy current sensor should not be construed as to limit the sensor to the direct detection of eddy currents.

That the eddy current sensor is arranged for pulsed operation means that the eddy current sensor is arranged to emit a pulse of current, for example, alternating current, when stationary or approximately stationary, and monitor the response of the well casing. The eddy current sensor may be arranged to be optimised for measuring the response of a cable or control line running alongside the outside of a well casing. In use, after a pulse has been emitted and analysed, the eddy current sensor may be rotated to a different position with respect to the well casing, and the pulse emitting process repeated.

The downhole tool may also comprise a control unit including a processing unit arranged to process the readings taken by the eddy current sensor.

Advantageously, the downhole tool may be inserted into a well bore, and the eddy current sensor deployed in contact with or in close proximity to the inner wall of the well casing. By rotating the eddy current sensor around the circumference of the internal wall of the well casing, the eddy current sensor may be used to detect the presence of a downhole cable or control line running along the external wall of the well casing. A downhole cable or control line is typically less than 0.5 inches (approximately 13 mm) in diameter and may be mild or stainless steel. A well casing thickness is typically in the range of 0.25 to 0.5 inches (approximately 6 mm to 13 mm) and the downhole cable or control line running along the external wall of a well casing will increase the amount of metal present in that particular section of the well casing. This increase in metal may be detected by the eddy current sensor, thereby indicating the presence of the control line. The downhole cable or control line is located at the outer of the well casing, and so will be further away from the eddy current sensor than the well casing. The applicant has developed an eddy current sensor, preferably a co-axial eddy current sensor, optimised to detect the tail portion, preferably the far tail portion, of the response curve measured following the pulsed operation of the eddy current sensor, and demonstrated that this far tail portion is representative of the material located furthest away from the eddy current sensor. Therefore, the applicant has determined that analysis of the tail portion of the response curve provides a measurement characteristic of material located furthest away from the eddy current sensor. In the case when a control line is present adjacent to the well casing, analysis of the tail of the response curve will indicate the presence of the control line.

The control unit may comprise a surface control unit. The control unit may comprise a downhole unit and a surface unit, the downhole unit and surface unit being in communication with each other. Such communication may be via a wireline, or wireless communication method. The control unit may be arranged to control the operation of the downhole tool. The downhole tool may comprise a telemetry cartridge. The telemetry cartridge may be arranged to send data signals between the eddy current sensor and the surface control unit. The downhole tool may be arranged to transmit eddy current sensor readings from the eddy current sensor to the control unit. The processing unit of the control unit is arranged to analyse the eddy current sensor readings and provide an indication of where additional metal, for example a control line, is detected at the well casing, particularly at the outer of the well casing. The control unit may comprise a memory unit arranged to record the location of any detected downhole cables or control lines. The data regarding the location of any detected downhole cables or control lines may be used to plan perforation patterns which do not damage the downhole cable or control line. The data regarding the location of any detected downhole cable or control lines may be used by a downhole tool arranged to perforate the well casing.

The eddy current sensor may comprise a receiver coil. The eddy current sensor may comprise a transmission coil. The eddy current sensor may comprise a ferrite core. The radius of the receiver coil may be less than the radius of the transmission coil. The receiver coil may have a greater number of turns than the transmission coil. The receiver coil and transmission coil may be configured in a nested arrangement. The coils of the transmission coil may be located within the coils of the receiver coil. Alternatively, the coils of the receiver coil may be located within the coils of the transmission coil. The receiver coil and transmission coil are preferably co-axial.

The downhole control unit may be configured to generate a series of timed electrical pulses to drive the transmission coil. The downhole control unit may be configured to sample the signal from the receiver coil after the sending of a pulse to the transmission coil. The downhole control unit may be configured to sample the signal from the receiver coil for a set period of time.

In addition to a rotational movement, the downhole tool may be configured to move the eddy current sensor in a longitudinal direction. The longitudinal direction may be parallel to the axis of rotation of the eddy current sensor. By rotation of the eddy current sensor and longitudinal movement of the eddy current sensor in between the pulsed operation of the eddy current sensor, the downhole tool may be used to detect downhole cable or control lines over a length of wall casing. The movement of the downhole tool may be such that a helical path is followed by the eddy current sensor as it rotates around and through a well casing. In an alternative embodiment, the sensor may rotate, in a stepped manner, a full 360 degrees around the inside wall of the well casing, and then be moved in a longitudinal direction. In addition to the rotational position of the eddy current sensor, the control unit may store information relating to the longitudinal position of the eddy current sensor. This information may be used to indicate both the angular position of a downhole cable or control line and also the longitudinal position of a downhole cable or control line. In many cases, a cable or control line will run the length of a well casing, in a fixed angular position. However, if this is not the case, then the invention provides an apparatus and method capable of detecting such a variation, either in the longitudinal extension of the cable or control line, or the angular position of the cable or control line.

The downhole tool may comprise a support arm, the eddy current sensor being located at a distal end of the support arm. The support arm may be under bias. The support arm may be under bias such that, in use, the eddy current sensor is pushed against the internal wall of the well casing. The support arm may include a spring. The eddy current sensor may comprise one or more rollers or skids, the rollers or skids configured to reduce friction with the internal wall of a well casing. Advantageously, such rollers allow the eddy current sensor to be moved more easily during operation of the downhole tool. The support arm may be movable between a first position and a second position. The first position may be such that the eddy current sensor is in contact with or proximate to the internal wall of the well casing. The second position may be such that the eddy current sensor is not proximate to the internal wall of a well casing. The first position may be used when the eddy current sensor is taking readings from the well casing. The second position may be used when the downhole tool is being lowered down the well into position, and it is desirable to reduce the frictional contact between the downhole tool and the well casing. The downhole tool may be configured such that the movement of the support arm between the first position and second position is automatic. For example, the support arm may be moved for a set period of time. Alternatively, the support arm may comprise a sensor to detect when the eddy current sensor comes into contact with or is proximate to the internal wall of the well casing. The sensor may, for example, be a pressure sensor or the eddy current sensor itself. Such an arrangement may allow for the downhole tool to be used in well casings of different internal diameters whilst providing a consistent contact between the eddy current sensor and inner wall of the well casing.

The invention provides, according to a second aspect, a method of detecting a downhole cable or control line running along the external wall of a well casing, comprising the steps of:

providing an eddy current sensor and locating the eddy current sensor in proximity to the internal wall of a well casing, sending a pulse of current to the eddy current sensor, thereby generating a magnetic field, and creating eddy currents in the well casing, measuring, using the eddy current sensor, the magnetic field generated by the eddy currents induced within the downhole cable or control line, moving the eddy current sensor around the circumference of the internal wall of the well casing, repeating the generating and measuring steps, analysing the measurement results of the eddy current sensor, wherein the analysis identifies any readings which present a profile suggestive of a downhole cable or control line, and recording the location corresponding to any such readings.

The pulse of current may be a pulse of alternating current. The analysis may be performed by a computer processing unit, the computer processing unit comprising a computer program.

The computer processing unit may be calibrated prior to deployment of the downhole tool. The calibration may comprise repeating the method steps on a well casing of known properties. For example, a calibration well casing may comprise a downhole cable or control line running along the external wall, disposed at a known angle and longitudinal displacement. The measurement results obtained for the well casing of known properties may be stored by the computer processing unit. The calibration process may provide a number of measurement results which may be compared to downhole measurement results as part of an analysis step.

The method may include the step of moving the eddy current sensor in a longitudinal direction. The longitudinal direction is preferably in the same direction as the longitudinal axis of the well casing.

The invention provides, according to a third aspect, a method of planning a perforation pattern for a well casing, the method comprising the steps of detecting the location of downhole cable or control lines running along the external wall of the well casing according to the method of the second aspect of the invention, and plotting a perforation pattern such that the perforations will not damage any of said downhole cable or control lines.

It will of course be appreciated that features described in relation to one aspect of the present invention may be incorporated into other aspects of the present invention. For example, the methods of the invention may incorporate any of the features described with reference to the apparatus of the invention and vice versa.

DESCRIPTION OF THE DRAWINGS

Embodiments of the present invention will now be described by way of example only with reference to the accompanying schematic drawings of which.

DETAILED DESCRIPTION

Figure 1:
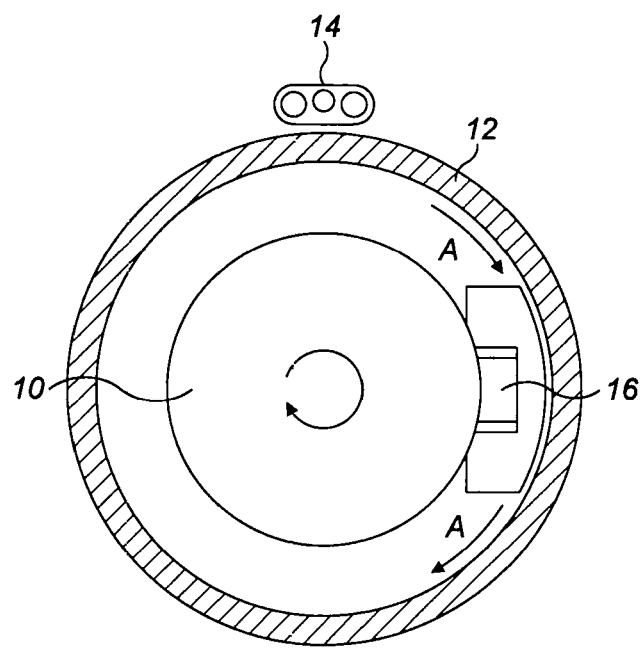
FIG. 1 shows a schematic view of a cross section of a downhole tool and well casing according to a first embodiment of the invention.

FIG. 1 shows a cross-section of a downhole tool 10 in situ, with a cylindrical well casing 12, a control line 14 located on the external wall of the well casing 12, and an eddy current sensor 16 in contact with the internal wall of the well casing 12. In an alternative arrangement the eddy current sensor may be proximate to the internal wall of the well casing 12, preferably located within 3 mm of the well casing. The eddy current sensor 16 is arranged to be rotated around the internal wall of the well casing 12, as indicated by the arrow A. Whilst FIG. 1 shows a control line, the skilled person will appreciate the described embodiment of the invention is equally capable of detecting a downhole cable or other external anomalies.

Figure 2:
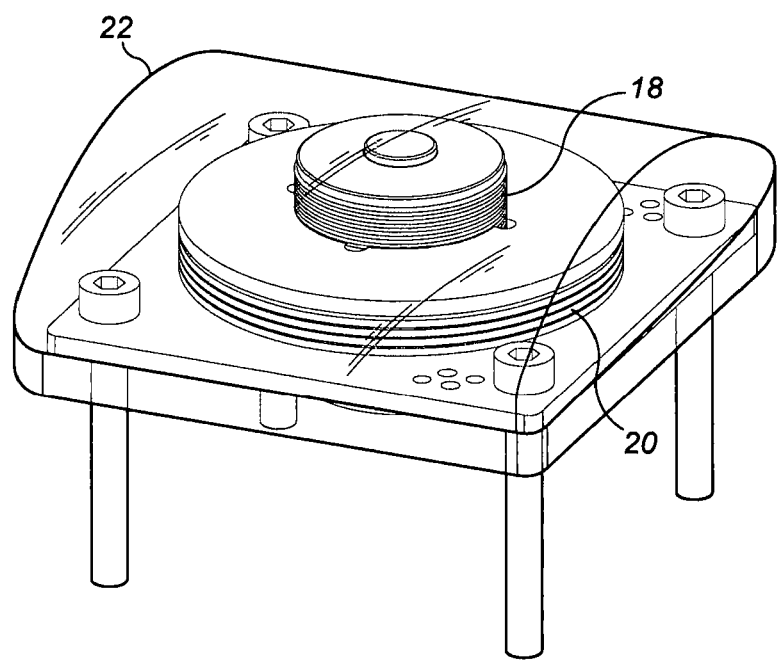
FIG. 2 shows a schematic representation of an eddy current sensor according to the first embodiment of invention.

FIG. 2 shows the eddy current sensor 16 in greater detail, with the eddy current sensor 16 comprising a receiver coil 18, a transmission coil 20, and an encapsulation material. The transmission coil 20 is a high current, low number of turns coil, and the receiver coil 18 is a low current, high number of turns coil with a ferrite core.

Figure 3:
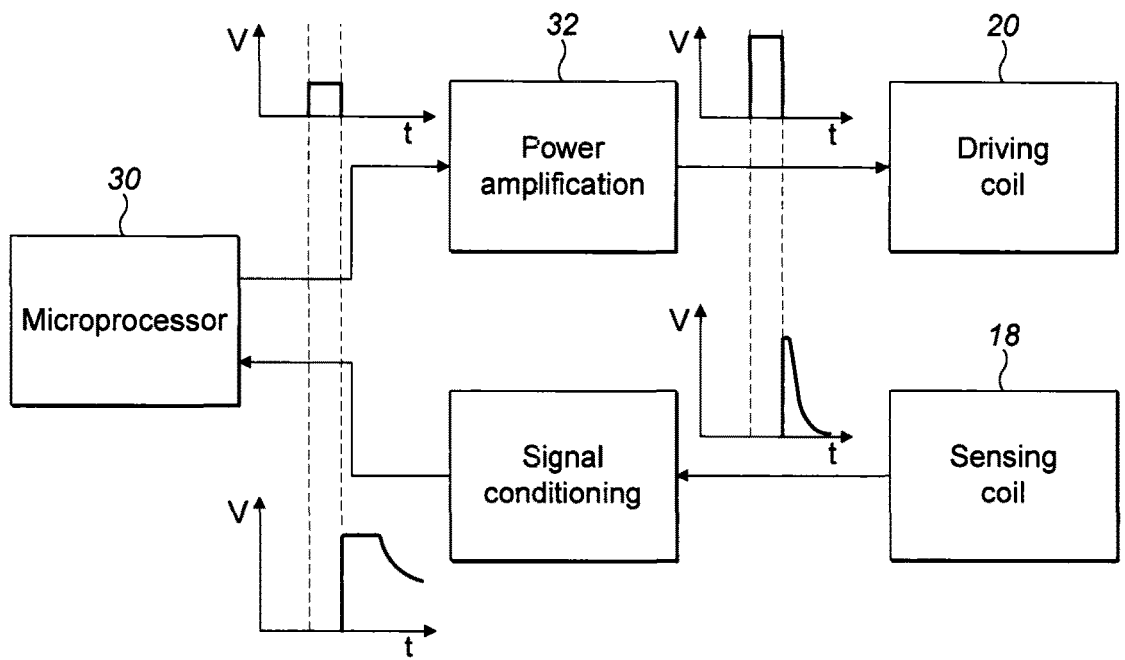
FIG. 3 shows a block diagram of the electronic operation of a downhole tool according to the first embodiment of the invention.
Figure 4:
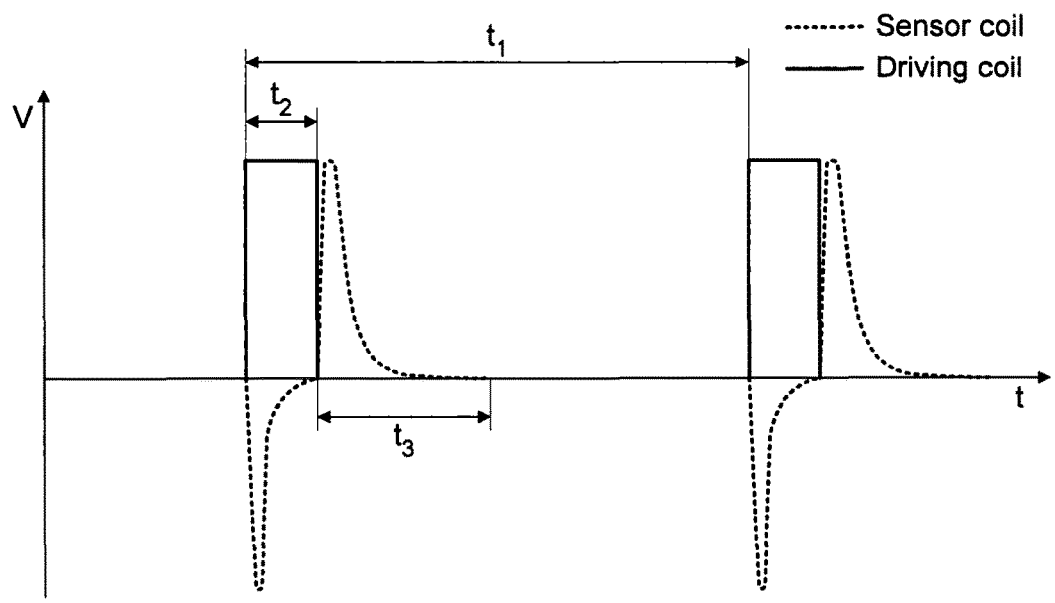
FIG. 4 shows an electronic timing diagram for the electronic operation of the downhole tool according to the first embodiment of the invention.

FIGS. 3 and 4 illustrate the overall electronic operation of the downhole tool 10. The downhole tool comprises a control unit 30 including a microprocessor generating a sequence of square wave pulses ($t_2$) that are amplified 32 and fed through to the transmitter coil 20 of the eddy current sensor 16. The control unit 30 also comprises an analogue-to-digital convertor (ADC) which is switched on at the end of the current pulse and which is arranged to sample the amplified signal detected by the receiver coil for a set period of time ($t_3$). As has been described, the tail end of the response curve is indicative of whether or not there is a cable or control line present, and the control unit is arranged to analyse the tail end of the response curve in particular. Each transmission and respective receiving step is undertaken with the tool stationary or approximately stationary. As the transmitting and receiving steps are undertaken, the downhole tool is being rotated within the well casing. The steps are repeated at regular intervals ($t_1$) until the tool has been rotated 360 degrees, in the desired number of increments.

Figure 5:
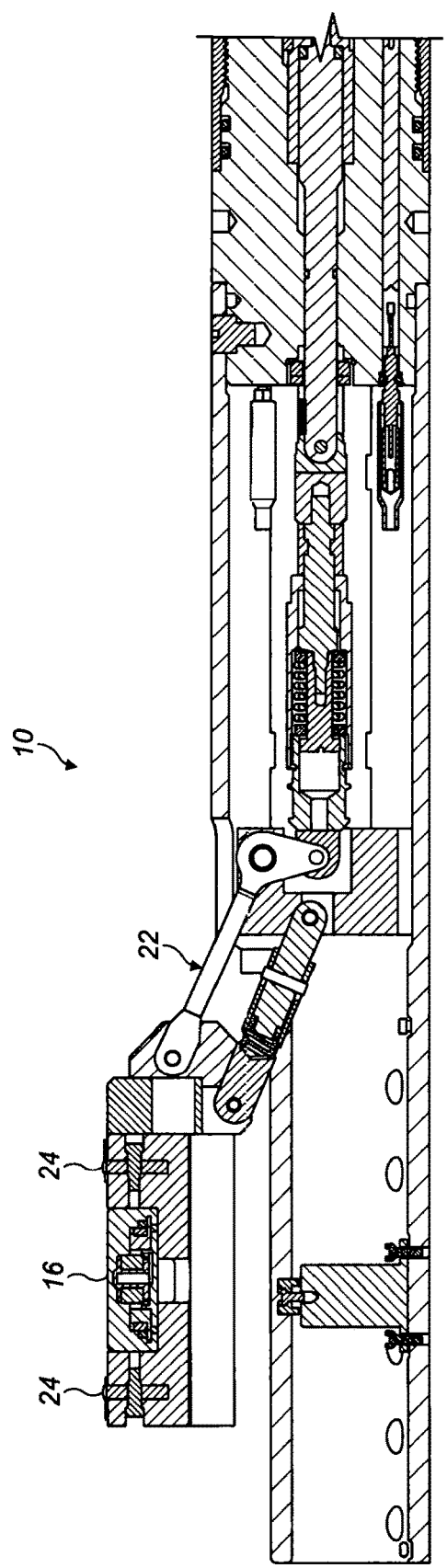
FIG. 5 shows a side view of a downhole tool according to the first embodiment of the invention.

FIG. 5 shows a cross-sectional view of the downhole tool 10. The eddy current sensor 16 is mounted on a spring loaded arm 22, which acts to bias the eddy current sensor 16 against the internal wall of the well casing. The support arm includes an actuator for controlling the position of the support arm. The eddy current sensor 16 also comprises rollers (or skids) 24 which act to reduce the frictional contact between the eddy current sensor 16 and the inner wall of the well casing, and also ensure a consistent spacing between the eddy current sensor 16 and the internal wall of the well casing. Ensuring a consistent spacing between the eddy current sensor and the internal wall of the well casing should provide more accurate measurements of the eddy currents created in the well casing and control line.

The operation of the downhole tool proceeds as follows. The downhole tool 10 is lowered into a well casing until in the appropriate vertical location. If necessary, the downhole tool may comprise support struts that are extended to stabilise the downhole tool 10 and centre the tool 10 within the well casing. A surface control unit may include tool settings appropriate to the well casing diameter and wall thickness, which are sent to the tool via an electronic communication means, preferably a control wire attached to a telemetry cartridge present downhole with the tool. During positioning, the support arm 22 is in a "retracted" position, such that the eddy current sensor is not proximate to the internal wall of the well casing. This makes lowering the downhole tool into position easier, and reduces the possibility of damaging the eddy current sensor whilst doing so. The support arm 22 is then moved into an "extended position", such that the eddy current sensor is in contact with or proximate to the internal wall of the well casing. The movement between the retracted and extended position is controlled by a sensor, which monitors the load experienced by the support arm, halting the movement of the arm when the eddy current sensor 16 is pushing against the internal wall of the well casing at a set force. In an alternative embodiment, the extension of the support arm 22 may be determined by the tool settings stored by the control unit.

Once the eddy current sensor 16 is in contact with the internal wall of the well casing, the eddy current sensor 16 begins the scanning process as set out above, generating eddy currents in the well casing and measuring the magnetic fields created by eddy currents in order to obtain an indication of the amount of metal in the well casing at any particular point.

The principles behind eddy current sensor operation are well known and have been discussed above. In summary, the eddy current detection works by creating eddy currents in the well casing by applying a varying magnetic field to the casing. The eddy currents create an opposing magnetic field which interacts with the magnetic field generated by the eddy current sensor. The depth of penetration of a varying magnetic field depends on the frequency of the magnetic field, which is known as the skin effect. The absence or presence of more or less metal in or in contact with or proximate to the well casing is detectable by monitoring the decay of the eddy currents created in the well casing. This is done by monitoring the opposing magnetic field generated by the eddy currents. As there is greater metal present when a control line runs along the outer wall of a well casing, the eddy current readings will differ to those of the well casing where there is no control line at the outside wall.

The use of square wave pulses to generate eddy currents is straightforward and reliable from the operational and electronic point of view. Also, this provides the benefit of allowing the generation and comparison of eddy current signals at and from different penetration depths simultaneously. The later in time parts of the eddy currents decay curve (which follow the leading or trailing edge of a square magnetic field pulse) correspond to the magnetic fields of the eddy currents at a greater depth penetration than the earlier parts of the decay curve, which correspond to the magnetic fields from the eddy currents at reduced depths of penetration.

Once the downhole tool 10 has scanned the desired section of well casing, the support arm 22 may move back into the retracted position, and the downhole tool may be removed from the well casing. The operator now has an indication of where control lines run along the outer wall of the well casing, and may plan the well operation accordingly.

Whilst the present invention has been described and illustrated with reference to particular embodiments, it will be appreciated by those of ordinary skill in the art that the invention lends itself to many different variations not specifically illustrated herein.

For example, in an alternative embodiment, the eddy current sensor may comprise a single transmission and receiving coil, with the sensor being controlled such that the coil alternates between transmission and receiving.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A downhole tool for the detection of downhole cable or control lines, the downhole tool comprising:
   an eddy current sensor, the eddy current sensor being arranged to be proximate to an internal wall of a well casing,
   wherein the eddy current sensor includes a receiver coil and a transmitter coil, where the receiver coil and the transmitter coil are configured in a nested arrangement, and
   wherein the eddy current sensor is arranged for pulsed operation whereby an electrical pulse is generated in the transmission coil so as to generate eddy currents in the internal wall of the well casing and the downhole cable or control lines, the receiver coil being arranged to detect a magnetic field generated by the eddy currents,
   a rotational mechanism to rotate the eddy current sensor, with an axis of rotation parallel with the longitudinal axis of the well casing, and
   a control unit including a processing unit arranged to:
   process readings taken by the eddy current sensor, monitor a decay of the magnetic field induced by the eddy currents generated by the electrical pulse, analyse a tail end of a response curve of the receiver coil readings obtained during the decay, and
   provide an indication of where downhole cable or control lines are detected at an outer wall of the well casing on the basis of the decay of the magnetic field.

2. A downhole tool as claimed in claim 1, wherein the control unit comprises a surface control unit.

3. A downhole tool as claimed in claim 1, the control unit being arranged to control the operation of the downhole tool.

4. A downhole tool as in claim 3, further comprising a telemetry cartridge.

5. A downhole tool as claimed in claim 4, wherein the telemetry cartridge is arranged to send data signals between the eddy current sensor and the control unit.

6. A downhole tool as claimed in claim 1, wherein the control unit comprises a memory unit arranged to record the location of any detected downhole cables or control lines.

7. A downhole tool as in claim 1, wherein the downhole tool is configured to move the eddy current sensor in a longitudinal direction.

8. A downhole tool as in claim 1, wherein the downhole tool comprises a support arm, the eddy current sensor being located at a distal end of the support arm.

9. A downhole tool as claimed in claim 8, wherein the support arm is under bias, such that, in use, the eddy current sensor is pushed against an inner wall of the well casing.

10. A downhole tool as claimed in claim 9, further comprising a sensor arranged to monitor the load experienced by the support arm, wherein the downhole tool is arranged to halt the movement of the support arm when the eddy current sensor is pushed against the internal wall of the well casing at a set force.

11. A downhole tool as in claim 9, wherein the eddy current sensor comprises one or more rollers or skids, the rollers or skids configured to reduce friction with the internal wall of the well casing.

12. A downhole tool as in claim 1, wherein the transmitter coil and the receiver coil are arranged to be fixed in position relative to one another.

13. A downhole tool as claimed in claim 1, wherein the receiver coil and the transmission coil are co-axial.

14. A downhole tool as claimed in claim 1, wherein the control unit is arranged to generate a pulse of current having a square waveform.

15. A method of detecting a downhole cable or control line running along an external wall of a well casing, comprising the steps of:
   providing an eddy current sensor and locating the eddy current sensor in proximity to an internal wall of the well casing,
   wherein the eddy current sensor includes a receiver coil and a transmitter coil, where the receiver coil and the transmitter coil are configured in a nested arrangement,
   sending a pulse of current to the eddy current sensor, thereby generating a magnetic field, and creating eddy currents in the well casing,
   measuring, using the eddy current sensor, the magnetic field generated by the eddy currents induced within the downhole cable or control line,
   moving the eddy current sensor around the circumference of the internal wall of the well casing,
   repeating the generating and measuring steps,
   analysing the measurement results of the eddy current sensor, including:
   processing the readings taken by the eddy current sensor,
   monitoring a decay of the magnetic field induced by the eddy currents generated by the electrical pulse,
   analysing a tail end of the magnetic field response curve of the eddy current sensor readings during the decay, wherein the analysis identifies any readings which present a profile suggestive of the downhole cable or control line; and providing an indication of where the downhole cable or control lines are detected at an outer wall of the well casing on the basis of the decay of the magnetic field created by the eddy currents, and recording the location corresponding to any such indications of where the downhole cable or control lines are detected.

16. A method as claimed in claim 15, wherein the analysis of eddy currents is performed by a computer processing unit, the computer processing unit comprising a computer program.

17. A method as claimed in claim 16, including the step of the eddy current sensor being calibrated prior to downhole deployment.

18. A method as claimed in claim 17, wherein the calibration comprises repeating the method steps on a well casing of known properties.

19. A method as in claim 18, including the step of moving the eddy current sensor in a longitudinal direction.

20. A method of planning a perforation pattern for a well casing, the method comprising the steps of detecting the location of downhole cable or control lines running along an external wall of the well casing according to the method as claimed in claim 15, and plotting a perforation pattern such that the perforations will not damage any of said downhole cable or control lines.

21. A method as claimed in claim 20, wherein the transmitted coil and the receiver coil are arranged to be fixed in position relative to one another.

22. A method as claimed in claim 15, wherein the transmitted coil and the receiver coil are arranged to be fixed in position relative to one another.

23. A method as claimed in claim 15, wherein the pulse of current is a square wave.

* * * * *